(12) United States Patent
Qiao et al.

(10) Patent No.: US 11,932,614 B2
(45) Date of Patent: Mar. 19, 2024

(54) METHOD FOR PREPARING DIAZOXIDE

(71) Applicant: SOOCHOW UNIVERSITY, Suzhou (CN)

(72) Inventors: Chunhua Qiao, Suzhou (CN); Yiwen Xu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 17/789,474

(22) PCT Filed: Dec. 29, 2019

(86) PCT No.: PCT/CN2019/129657
§ 371 (c)(1),
(2) Date: Jun. 27, 2022

(87) PCT Pub. No.: WO2021/134143
PCT Pub. Date: Jul. 8, 2021

(65) Prior Publication Data
US 2023/0033450 A1 Feb. 2, 2023

(51) Int. Cl.
*C07D 285/24* (2006.01)

(52) U.S. Cl.
CPC .................... *C07D 285/24* (2013.01)

(58) Field of Classification Search
CPC .................................................... C07D 285/24
See application file for complete search history.

(56) References Cited

FOREIGN PATENT DOCUMENTS

CN       110903264 A       3/2020

OTHER PUBLICATIONS

Antony N. Shaw et al., "Substituted benzothiadizine inhibitors of Hepatitis C virus polymerase" Bioorganic & Medicinal Chemistry Letters 19 (2009) 4350-4353 (May 28, 2009).

Zongjie Gan et al., "Imidazolium chloride-catalyzed synthesis of benzimidazoles and 2-substituted benzimidazoles from o-phenylenediamines and DMF derivatives" Tetrahedron 74 (2018) 7450-7456 (Nov. 17, 2018).

Smail Khelili et al. "Synthesis and pharmacological evaluation of 1, 2, 4-benzothiadiazin-1, 1-dioxides bearing 5- or 7-sulfonylurea moieties" Medicinal Chemistry Research, vol. 12, Nr.:9, pp. 457-470 (Dec. 31, 2003).

*Primary Examiner* — Paul V Ward
(74) *Attorney, Agent, or Firm* — SZDC Law PC

(57) ABSTRACT

A method for preparing diazoxide includes reacting o-aminobenzenesulfonamide with N-chlorosuccinimide in a chlorine solvent to obtain 2-amino-5-chlorobenzenesulfonamide, mixing the 2-amino-5-chlorobenzenesulfonamide, an imidazole salt and an amide solvent, then heating same for reaction so as to obtain diazoxide; or mixing o-aminobenzenesulfonamide, an imidazole salt and an amide solvent, then heating same for reaction to obtain a compound IV; then reacting the compound IV with N-chlorosuccinimide in a chlorine solvent to obtain diazoxide. The application of imidazole hydrochloride as a catalyst in preparing diazoxide is also disclosed. The present invention avoids the use of highly corrosive and toxic chlorosulfonyl isocyanate, a strong acid (sulfuric acid), and a high reaction temperature (240-250° C.), and the reaction steps are short; the total yield of the two steps is more than 90%, and compared with publicly disclosed preparation methods for diazoxide, the synthesis route overcomes numerous shortcomings, thus being more suitable for industrial production.

4 Claims, 4 Drawing Sheets

METHOD FOR PREPARING DIAZOXIDE

This application is the National Stage Application of PCT/CN2019/129657, filed on Dec. 29, 2019, which is incorporated by reference for all purposes as if fully set forth herein.

TECHNICAL FIELD

The invention relates to compound synthesis technology, in particular to a method for preparing diazoxide.

BACKGROUND TECHNIQUE

Diazoxide is an antihypertensive drug, first aid drug for patients in hypertensive crisis. At the same time, it also used to a drug to treat hypoglycemia symptoms caused by hyperinsulinemia, especially the drug of choice for congenital hyperinsulinemia. It is a rare and urgently needed drug in clinical practice disease for infants which is not currently available in China. Molecular formula: $C_8H_7C_1N_2O_2S$, chemical names: diazoxidum; 7-chloro-3-methyl-2H-1,2,4-benzothiadiazine 1,1-dioxide; Hypertonalum; Hyperstat; 7-chloro-3-Methyl-2 hydrogen-1,2,4-benzothiadiazine 1,1-dioxide; CAS: 364-98-7. The chemical structure is shown as follows:

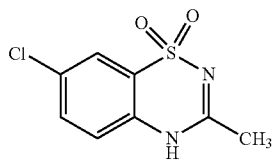

There were three reported synthesis routes A, B, C to prepare this drug.

The synthesis routes A, B use p-aminoaniline as the raw material. They both need conditions with high active, high corrosive reagents, high temperature, and anhydrous environment. Route C uses triethyl orthoacetate for the ring-closing reaction and reflux in ethanol for one-step ring-closing to obtain the product. Problems with existing methods: among the three routes, the steps of routes A and B are long. Route A requires a three-step reaction, and sulfurisocyanatidic chloride is used in the process. This reagent is toxic, extremely active, water-sensitive, and is reacting. Gas is released and the reaction is violent. The reagent $AlCl_3$ used in the next step is also easy to absorb moisture. Therefore, the anhydrous conditions of the reaction are strictly required. The final step requires the use of acetic acid. The final product is processed at a high temperature of 130° C. Acetic acid has strong volatility, irritating and corrosive. Route B requires four steps to obtain the final product, the first two steps are the same as route A, then the ring is opened after treatment with strong acid $H_2SO_4$, and then the product is obtained by ring-closing reaction with triethyl orthoacetate. Compared with route A, this route has an additional step of reaction and uses strong corrosive sulfuric acid. Route C requires acid binding agent and high temperature ring closure. Therefore, it is necessary to develop a new method for preparing diazoxide to use stable raw materials, reduce operation steps, and choose milder reagents to avoid the use of strong acids, so as to prepare azodiazine in high yield.

Technical Problem

The object of the present invention to provide a novel method for preparing diazoxide in which synthesis procedure is shorter, the reagent is easier to obtain, reaction conditions are milder, yield is higher, and it is a synthesis route suitable for industrialization.

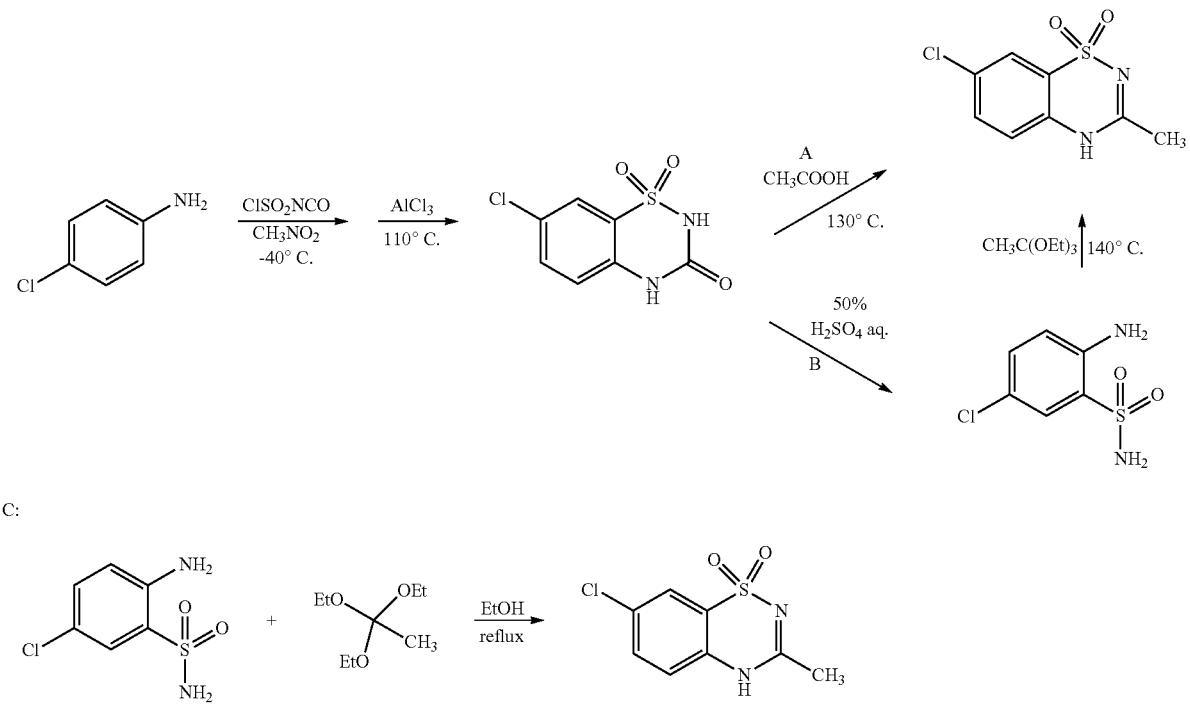

C:

The present invention provides a novel method for preparing diazoxide, which avoids using chlorosulfonyl isocyanate, strong acid (sulfuric acid), high reaction temperature (from 240 to 250° C.), and the reaction steps are short, the total yield can reach at 90%. And compared with the two reported methods for preparing diazoxide, the synthesis route provided by the present invention overcomes numerous shortcomings, therefore more suitable for industrial production.

Technical Solutions

In order to achieve the above-mentioned object of the invention, the technical solution adopted by the present invention is:

A method for preparing a diazoxide includes the following steps: mixing and heating 2-amino-5-chlorobenzenesulfonamide, an imidazolium salt and an amide solvent to obtain the diazoxide.

The present invention discloses an application of imidazole hydrochloride as a catalyst in the preparation of diazoxide.

The present invention discloses the 2-amino-5-chlorobenzenesulfonamide is synthesized by mixing o-aminobenzenesulfonamide and N-chlorosuccinimide in a chlorine solvent. Preferably, the reaction is under reflux, and a reaction time is between 2-6 hours.

In the above technical schemes, the imidazolium salt is imidazole hydrochloride; an amount of the imidazolium salt is 1-12 mol % of the 2-amino-5-chlorobenzenesulfonamide; preferably between 3-10 mol %; more preferably 5-7 mol %; and most preferably 5 mol %.

A method for preparing diazoxide includes the following steps: mixing and heating o-aminobenzenesulfonamide, an imidazolium salt and an amide solvent to obtain a compound IV; reacting the compound IV with N-chlorosuccinimide in a chlorine solvent to obtain diazoxide. Preferably, the reaction in the chlorine solvent is under reflux for 8-10 hours. The chlorine solvent is dichloromethane or chloroform.

In the above technical schemes, the imidazolium salt is imidazole hydrochloride; an amount of the imidazolium salt is 1-12 mol % of the 2-amino-5-chlorobenzenesulfonamide; preferably 3-10 mol %; more preferably 5-7 mol %; most preferably is 5 mol %.

In the present invention, the amide solvent is N,N-dimethylacetamide and the reaction is carried out between 120° C. and a reflux temperature, and a reaction time is 5-50 hours. Preferably at the reflux for 6 to 8 hours.

In the present invention, after heating reaction, the reaction solution is distilled and purified by column chromatography to obtain diazoxide or 3-methyl-2H-1,2,4-benzothiadiazine 1,1-dioxide (Compound IV).

In the present invention, the chlorine solvent is dichloromethane or chloroform; after the reaction, the pure product can be prepared by column chromatography purification or recrystallization.

A novel method for preparing diazoxide uses N, N-dimethylacetamide, and in the presence of an imidazolium salt, obtains the product in high yield. N, N-Dimethylacetamide is common solvent in industry. Compared with triethyl orthoacetate used in route C of the report synthesis of diazoxide, N, N-Dimethylacetamide is more stable, nonflammable, cheaper in price, and higher yield by this step, more than 95%.

The specific reaction is as follows: synthesis routes D or E:

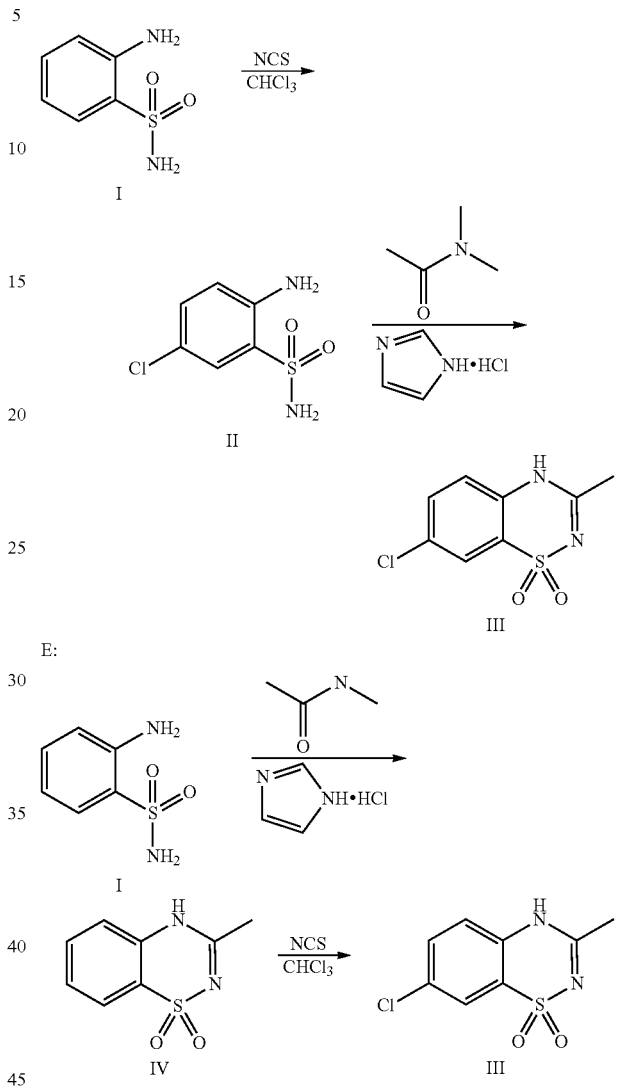

The characteristic of the synthesis route D: starting with reacting anthranilamide (I) and N-chlorosuccinimide (NCS), in dichloromethane (DCM) or trichloromethane, and obtaining compound (II) (2-amino-5-chlorobenzenesulfonamide), a yield between 85% and 90%; reacting compound (II) and N, N-Dimethylacetamide in the presence of an imidazolium salt to obtain diazoxide (III), a yield is between 90% and 98%. Or, the synthesis route E: staring with reacting anthranilamide (I) and N, N-dimethylacetamide in the presence of an imidazolium salt to obtain compound (IV), a yield between 90% and 98%; reacting the compound (IV) and N-chlorosuccinimide (NCS), in dichloromethane (DCM) or trichloromethane, obtaining diazoxide (III), a yield between 85% and 90%.

DETAILED DESCRIPTION

The method for preparing diazoxide disclosed by the present invention is as follow:

Mixing and heating 2-amino-5-chlorobenzenesulfonamide, imidazolium salt and amide solvent to obtain diazoxide. Alternatively, 2-amino-5-chlorobenzenesulfonamide is synthesized by mixing o-aminobenzenesulfonamide and N-chlorosuccinimide in a chlorine solvent

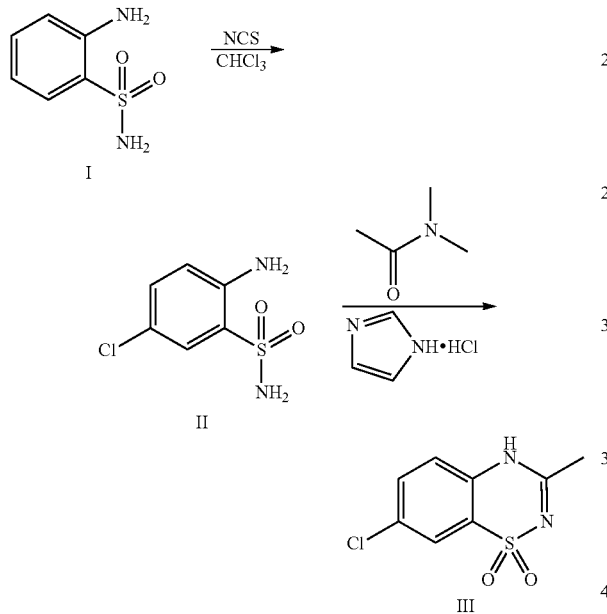

Or, mixing and heating o-aminobenzenesulfonamide, imidazolium salt and amide solvent to obtain compound IV; reacting the compound IV and N-chlorosuccinimide in chlorine solvent to obtain diazoxide.

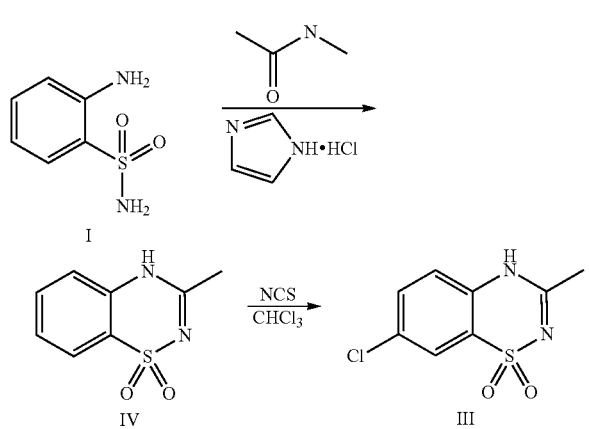

The products of all examples were extracted with ethyl acetate and purified by column chromatography mixed with solvent of ethyl acetate/petroleum ether in a volume ratio of 1:1 was used as eluent, $R_f$: 0.3.

Example 1

Mixing o-aminobenzenesulfonamide (1.72 g) and NCS (1.32 g, 1.0 equivalent), dissolving in dichloromethane (DCM), and stirring at reflux for about 5 h, removing the solvent DCM under reduced pressure, and purifying the residue with silica gel chromatography to obtain compound II, 2-amino-5-chlorobenzenesulfonamide (1.75 g), a yield of 85%, a purity of greater than 99%. Mass spectrum of compound: calculated value $[M+H]^+$ $C_6H_8ClN_2O_2S$, 206.99; experimental value: 206.83.

Figure 1:
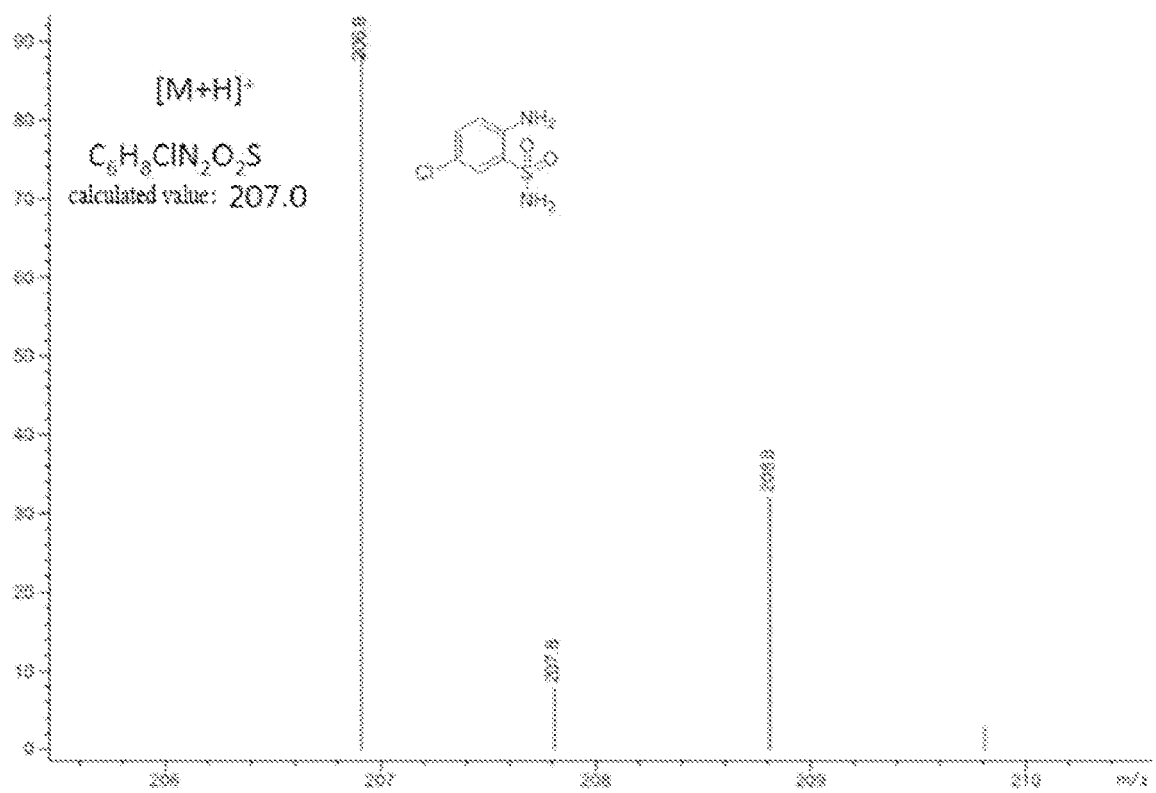
FIG. 1 shows the mass spectrum of 2-amino-5-chlorobenzenesulfonamide prepared by the present invention.

Mixing o-aminobenzenesulfonamide (1.7 2 g) and NCS (1.32 g, 1.0 equivalent), dissolving in trichloromethane, and stirring at reflux for about 3 h, and purifying the residue with silica gel chromatography to obtain the compound II, 2-amino-5-chlorobenzenesulfonamide (1.96 g), a yield of 95%, and a purity of greater than 99%. Mass spectrum experimental value: 206.9, the mass spectrum is shown in FIG. 1.

Example 2

2-Amino-5-chlorobenzenesulfonamide (2.05 g) and imidazole hydrochloride (0.14 g, 10 mol %) were added into N,N-dimethylacetamide (0.008 g), and the mixture was stirred at 120° C. for 48 h. The reaction solution was distilled to recover the excess N,N-dimethylacetamide, and the residue was purified with flash column chromatography on silica gel to obtain compound III diazoxide (2.07 g), a yield of 90%, and a purity of greater than 99%. Mass spectrum experimental value: 230.8.

Example 3

2-Amino-5-chlorobenzenesulfonamide (2.05 g) and imidazole hydrochloride (0.11 g, 7 mol %) were added into N,N-dimethylacetamide (0.008 g), and the mixture was stirred at 150° C. for 16 h. The reaction solution was distilled to recover the excess N,N-dimethylacetamide, and the residue was purified with flash column chromatography on silica gel to obtain compound III diazoxide (2.17 g), a yield of 94%, and a purity of greater than 99%. Mass spectrum experimental value: 230.9.

Example 4

Figure 2:
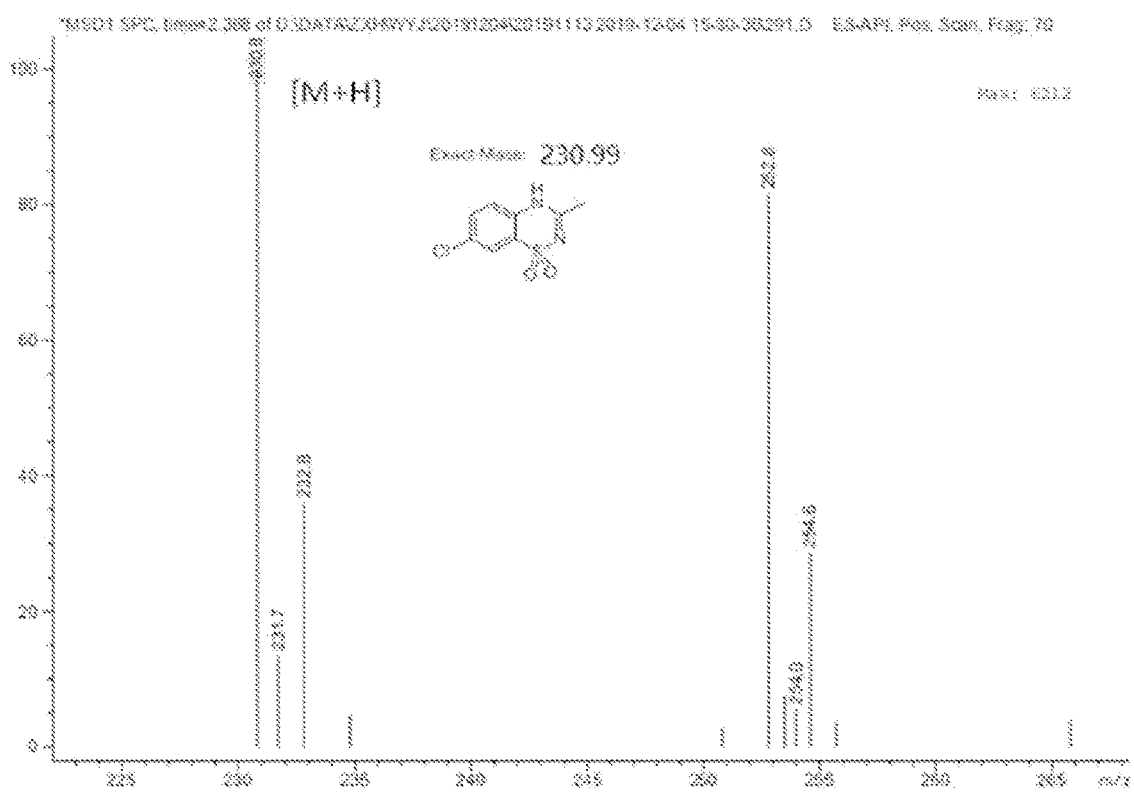
FIG. 2 shows the mass spectrum of diazoxide prepared by the present invention.
Figure 3:
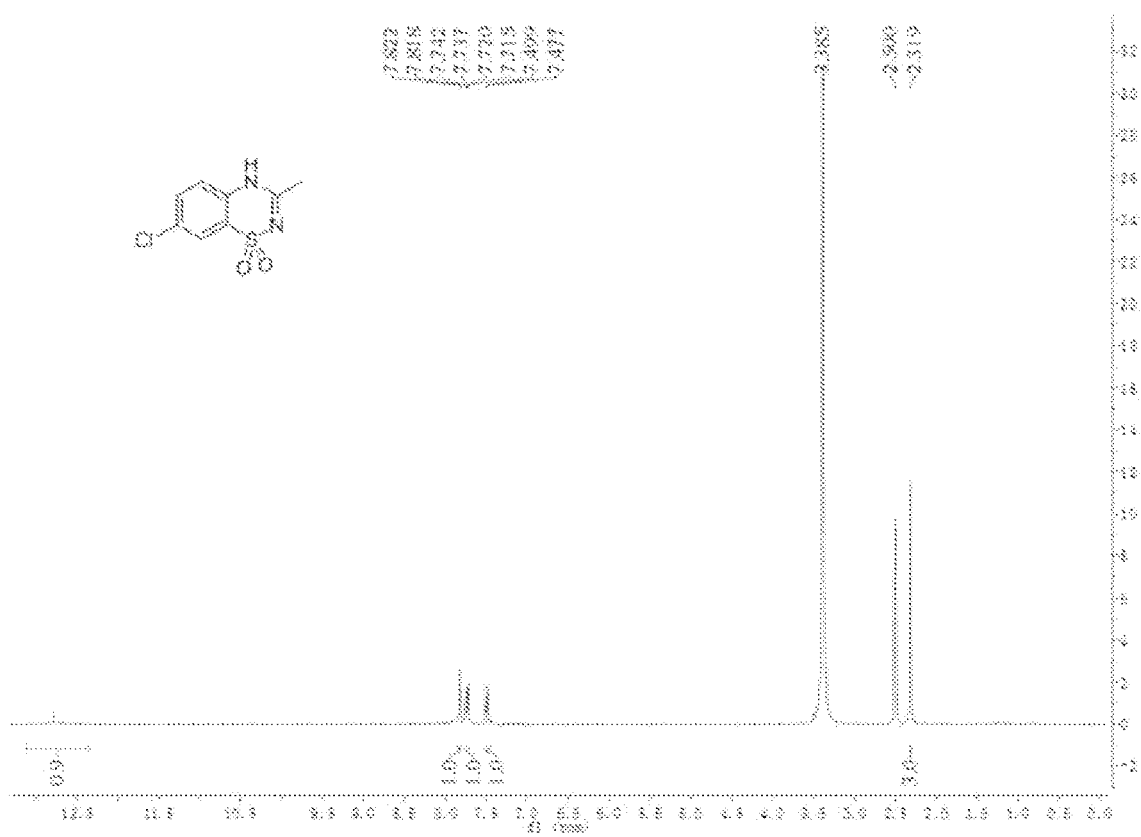
FIG. 3 shows the ¹HNMR spectrum of diazoxide.

2-Amino-5-chlorobenzenesulfonamide (2.05 g) and imidazole hydrochloride (0.08 g, 5 mol %) were added into N,N-dimethylacetamide (0.008 g), and the mixture was stirred at reflux for 7 h. The reaction solution was distilled to recover the excess N,N-dimethylacetamide, and the residue was purified with flash column chromatography on silica gel to obtain compound III diazoxide (2.26 g), a yield of 98%, and a purity of greater than 99%. The mass spectrum and ¹H NMR of diazoxide are shown in FIG. 2 and FIG. 3, respectively. The characterization of compound (III): mass spectrum of compound: calculated value $[M+H]^+$ $C_8H_8ClN_2O_2S$, 230.99; experimental value: 230.8. ¹HNMR (400 MHz, $CDCl_3$): 12.70 (br, 1H, NH), 7.82 (d, J=1.6 Hz 1H), 7.74 (dd, J=2.0, 8.8 Hz, 1H), 7.48 (d, J=8.8 Hz, 1H), 2.32 (s, 3H).

When the solvent was changed from N,N-dimethylacetamide to DMF, and other conditions remained the same, the product diazoxide could not be obtained.

Figure 4:
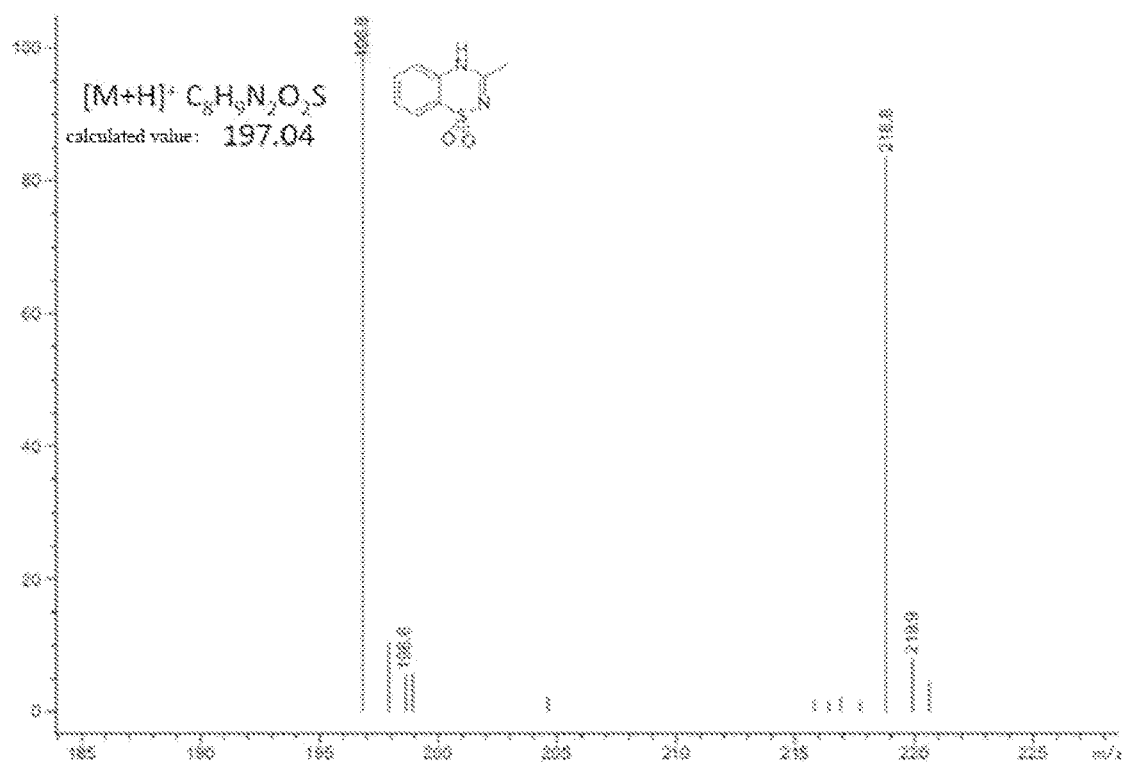
FIG. 4 shows the mass spectrum of compound (IV) prepared by the present invention.
Figure 5:
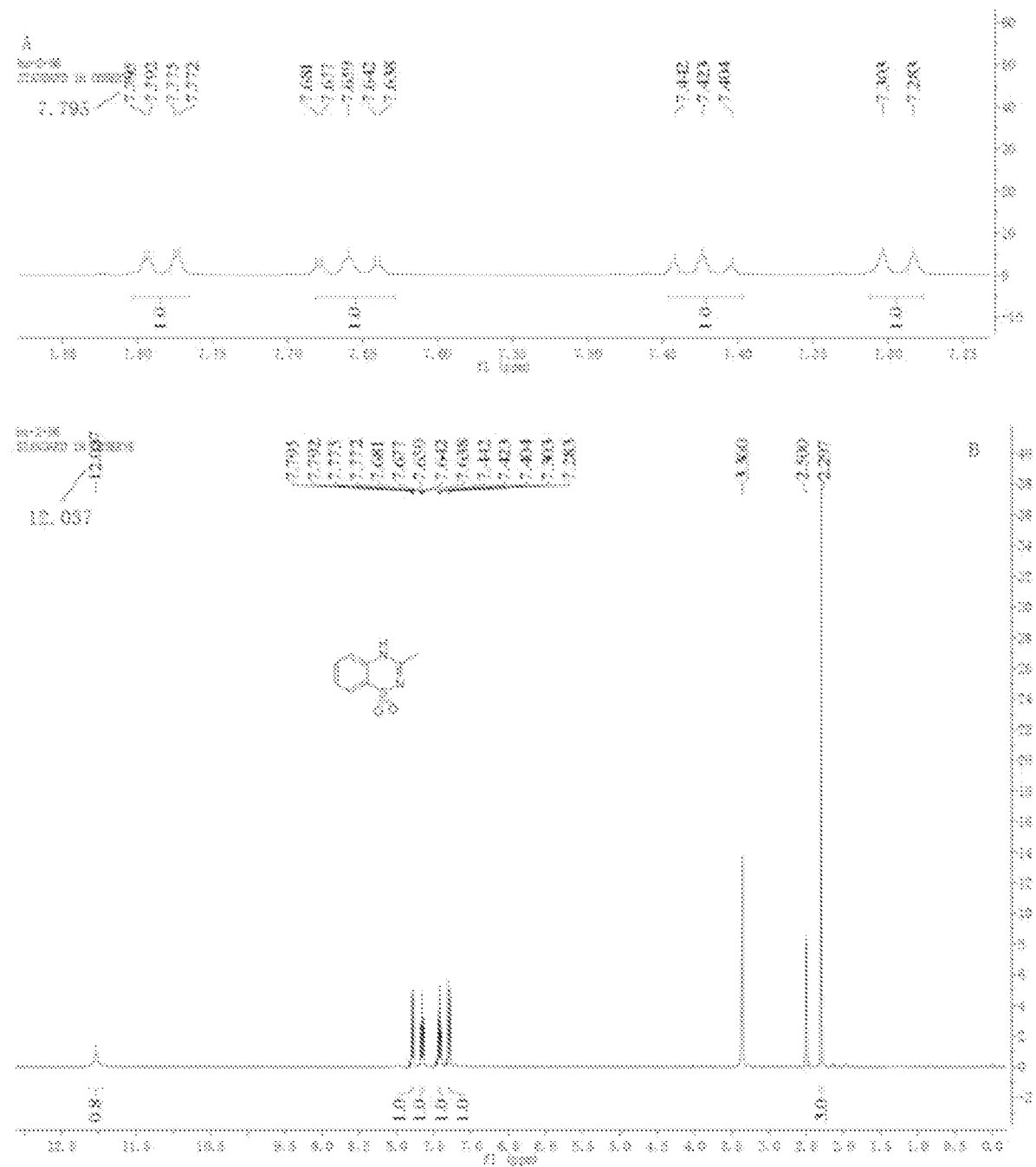
FIG. 5 shows the ¹HNMR spectrum of compound (IV)

Example 5 o-Aminobenzenesulfonamide (1.72 g) and imidazole hydrochloride (0.08 g, 5 mol %) were added into N,N-Dimethylacetamide (0.008 g), and the mixture was stirred at reflux for 6 h. The reaction solution was distilled to recover the excess N,N-dimethylacetamide, and the residue was purified with flash column chromatography on silica gel to obtain compound IV (1.84 g), a yield of 94%, and a purity of greater than 99%. The mass spectrum is shown in FIG. 4, experimental value: 196.8, calculated value: 197.04. $^1$HNMR of compound IV: $^1$HNMR (400 MHz, CDCl$_3$): δ 12.09 (br, 1H), 7.79 (dd, J=1.2 Hz, 8.0 Hz, 1H), 7.67 (dt, J=1.6 Hz, 7.6 Hz, 1H), 7.42 (t, J=7.6 Hz, 1H), 7.29 (d, J=8.0 Hz, 1H), 2.3 (s, 3H), as shown FIG. 5. Part A of FIG. 5 is a partially enlarged view of part B of FIG. 5.

The chemical structure is shown as follows:

IV

Figure 6:
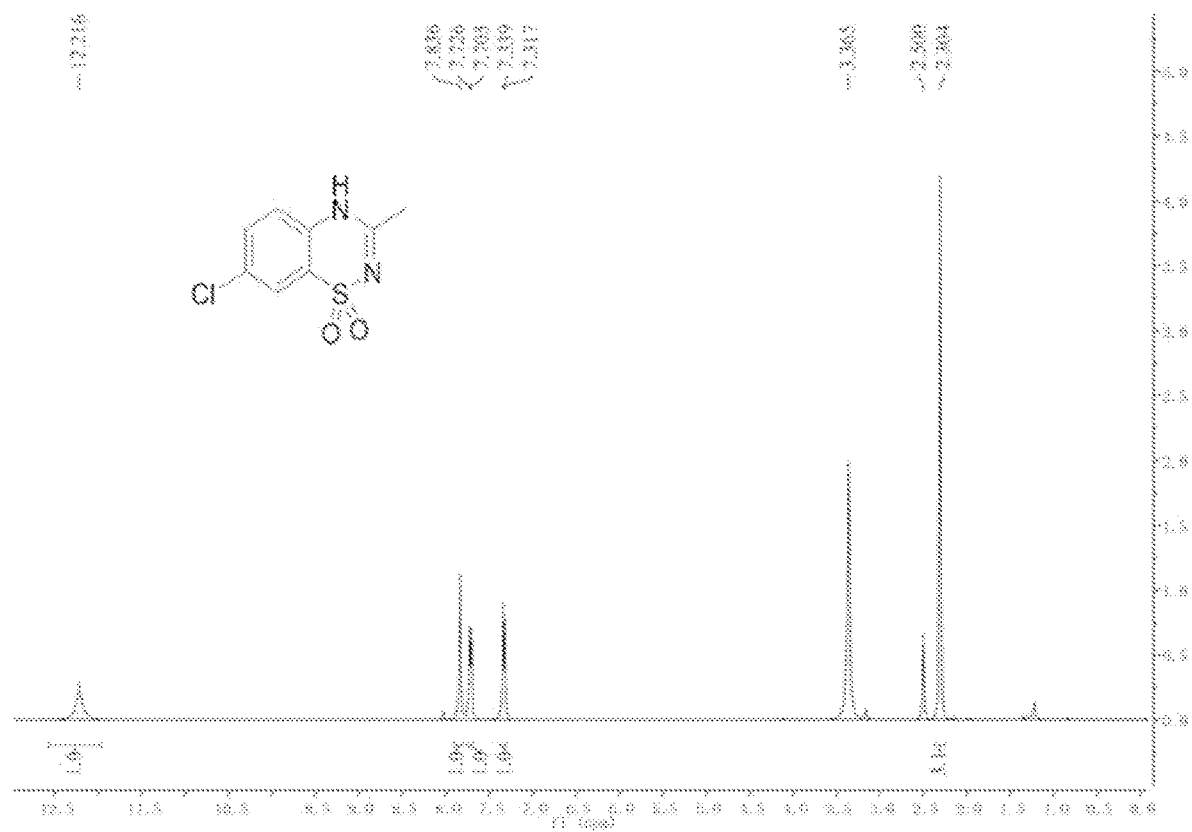
FIG. 6 shows the ¹H NMR spectrum of diazoxide.

A mixture of compound IV (1.96 g) and NCS (1.32 g, 1.0 equivalent) in trichloromethane was stirred at reflux for about 9 h, and then purified by column chromatography to obtain the product diazoxide (III), 2.06 g, a yield of 90%, a purity of greater than 99%, the experimental value: 230.9; the $^1$HNMR spectrum is shown in FIG. 6.

If the solvent was changed from N,N-dimethylacetamide to DMF, and other conditions remained the same, the product compound IV could not be obtained.

Example 6 o-Aminobenzenesulfonamide (1.72 g) and imidazole hydrochloride (0.11 g, 7 mol %) were added into N,N-dimethylacetamide (0.008 g), and the mixture was stirred at 140° C. for 15 h. The reaction solution was distilled to recover the excess N,N-dimethylacetamide, and the residue was purified with flash column chromatography on silica gel to obtain compound IV (1.76 g), a yield of 90%. A mixture of compound IV (1.96 g) and NCS (1.32 g, 1.0 equivalent) in trichloromethane was stirred at reflux for about 10 h, and then purified by column chromatography to prepare the product diazoxide (III), 2.07 g, a yield of 90%, a purity of greater than 99%, the experimental value: 231.1.

The invention claimed is:

1. A method for preparing a diazoxide, comprising the following steps:
   mixing and heating o-aminobenzenesulfonamide, an imidazolium salt and an amide solvent to obtain a compound IV; reacting the compound IV with N-chlorosuccinimide in a chlorine solvent to obtain the diazoxide,
   wherein the compound IV has the following structure:

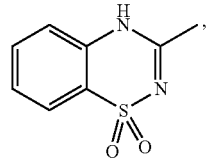

IV and the diazoxide has the following structure:

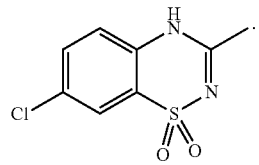

2. The method of claim 1, wherein the imidazolium salt is imidazole hydrochloride; an amount of the imidazolium salt is 1-12 mol % of the 2-amino-5-chlorobenzenesulfonamide; the amide solvent is N,N-dimethylacetamide and the reaction is carried out between 120° C. to a reflux temperature, and a reaction time is 5-50 hours.

3. The method of claim 2, wherein the amount of the imidazolium salt is 3-10 mol % of the 2-amino-5-chlorobenzenesulfonamide; the reaction is carried out under reflux for 6-8 hours.

4. The method of claim 1, wherein the reaction in the chlorine solvent is under reflux for 8-10 hours; the chlorine solvent is dichloromethane or chloroform.

* * * * *